United States Patent [19]

Berkowitz et al.

[11] 4,410,710

[45] Oct. 18, 1983

[54] CONVERSION OF IRIDOIDS TO PROSTAGLANDINS

[75] Inventors: William F. Berkowitz, Queens, N.Y.; Satish C. Choudhry, Corvallis, Oreg.; Joseph A. Hrabie, Atlanta, Ga.

[73] Assignee: Research Foundation of the City University of New York, New York, N.Y.

[21] Appl. No.: 305,601

[22] Filed: Sep. 25, 1981

[51] Int. Cl.$^3$ ............................................. C07D 307/93
[52] U.S. Cl. ..................................... 549/312; 536/4.1; 536/18.1; 549/298; 549/299
[58] Field of Search ................... 260/343.3 P; 549/312

[56] References Cited

PUBLICATIONS

Berkowitz et al., J. Org. Chem., 1982, 47, 824–829.
Berkowitz et al., (I) Tetrahedron Letters, No. 19, pp. 1641–1644, 1979.
Naruto et al., Tetrahedron Letters, No. 3, pp. 251–254, 1979.
Berkowitz et al., (II) Tetrahedron Letters, vol. 22, pp. 1075–1076, 1981.
Fieser & Fieser, Reagents for Organic Synthesis, vol. 4, p. 151.

Primary Examiner—Jane T. Fan
Attorney, Agent, or Firm—John S. Roberts, Jr.

[57] ABSTRACT

Naturally occurring iridoids provide the starting material for a unique synthesis sequence to produce prostaglandin intermediates. The iridoid lactone is hydrogenated, converted to an acetal, and rings opened to introduce the carbonyl octenyl side chain in six steps. The intermediate can be converted to prostaglandin as previously demonstrated.

3 Claims, No Drawings 4,410,710

CONVERSION OF IRIDOIDS TO PROSTAGLANDINS

This work was performed under City University of New York, financial assistance FRAP 11424.

Prior Art

The inventors have reported chiral prostanoid intermediates from aucubin in *Tetrahedron Letters* No. 19, pp. 1641–1644 (1979).

The conversion of Asperuloside to an optically active prostaglandin intermediate is reported in *Tetrahedron Letters*, Volume 22, pp. 1075–1076 (1981).

The conversion of prostaglandin intermediate to prostanoids is shown in (M. Naruto, K. Ohno, M. Naruse and H. Takeuchi *Tett. Lett.* 251 (1979); M. Naruto, K. Ohno and N. Naruse *Chem. Lett.* 1419 (1978); and M. Naruto, K. Ohno, N. Naruse and H. Takeuchi *Chem. Lett.* 1423 (1979)).

BACKGROUND OF THE INVENTION

The starting materials for the novel synthesis of prostaglandin intermediates disclosed herein are iridoid glycosides. These are a group of naturally occurring compounds characterized by the cyclopentanopyran ring system shown and numbered below

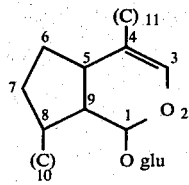

In all of the compounds, a β glucosyloxy group (indicated as glu) is present on C-1 and a double bond between C-3 and C-4, giving rise to the characteristic enol ether. C-10 and C-11 may or may not be present. In the plumieride series four additional carbons are present attached to C-10. The compounds are further characterized by the presence of several oxygen functions in the aglucone. These may be hydroxyl groups, alkoxyl groups, acyloxy groups or epoxides. A double bond is frequently present in the cyclopentane ring. These various combinations have given rise to about 27 known glucosides and some 15 related nonglucosidic substances.

The 10 carbon aglucones are of particular interest in the present invention. These include asperuloside, deacetylasperuloside, paederoside (these all have the closed 5 membered ring between C-4 and C-6 on the basic iridoid system. Scandoside, daphylloside and paederosidic acid lack ring closure. The ring may be closed subsequently.

The structures are shown below.

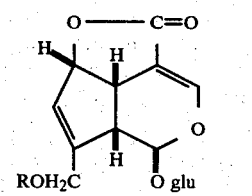

asperuloside, R = acetyl
deacetylasperuloside, R = H

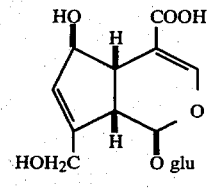

scandoside

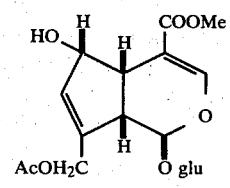

daphylloside

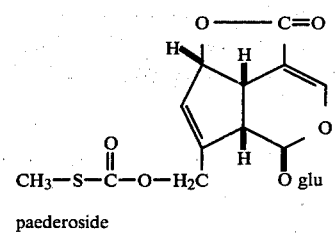

paederoside

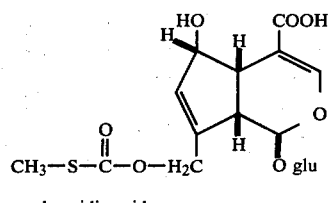

paederosidic acid

Isolation is generally affected by (a) adsorption and elution from charcoal, (b) the use of lead acetate as a clarifying agent and (c) direct Soxhlet extraction with an organic solvent. The plant extracts are available from Hines Wholesale Nurseries, Santa Ana, Calif. and Strybing Arboretum, San Francisco, Calif.

SUMMARY OF THE INVENTION

A useful prostaglandin intermediate, 1a-[3aR,4S,5R,6aS]hexahydro-5-(hydroxymethyl)-4-[(E)-3-oxo-1-octenyl]-2H-cyclopenta [b]furan-2-one acetate is prepared from asperuloside. The following description is shown schematically below. Ohno and coworkers (M. Naruto, K. Ohno, M. Naruse and H. Takeuchi *Tett. Lett.* 251 (1979); M. Naruto, K. Ohno and N. Naruse *Chem. Lett.* 1419 (1978); and M. Naruto, K. Ohno, N. Naruse and H. Takeuchi *Chem. Lett.* 1423 (1978)) above have recently converted benzoate 1b into PGF$_{2\alpha}$ and 11-homo PGF$_{2\alpha}$. The use of similar procedures should allow the conversion of the acetate to the same prostanoids. Crude asperuloside was isolated from Coprosma repens, obtained from Hines Wholesale Nurseries, Santa Ana, Calif. and Strybing Arboretum, San Francisco, Calif. The procedure of Briggs (L. H. Briggs and G. A. Nicholls, J.C.S. 3940 (1954) was used to isolate the crude asperuloside and it was converted to its tetraacetate 2b (acetic anhydride/pyridine). This was purified by a combination of chromatography and crystallization and afforded pure tetraacetate, m.p. 150°–151° C. (lit. m.p. 154° C.) in 0.2% yield based on the weight of fresh plant material.

The tetraacetate 2b was hydrogenated over 5% Rhodium on carbon in ethyl acetate at 1 atm. by starting at −30° C. and raising the temperature slowly to 0° C. during 3 hrs. Tetrahydroasperulosidetetraacetate (3) m.p. 148°–9° C. was isolated in virtually quantitative yield. Partial hydrolysis of 3 in refluxing AcOH/H$_2$O (5/1) for three hours afforded a mixture of tetracyclic acetal 4 (m.p. 113°–4° C., $[\alpha]_D^{25}$ −61.5° (chloroform)) and hemiacetal 5, m.p. 151°–2° C. When the hydrolysis was continued for 8 days at 100°–110° C., acetal 4 was produced in 86–92% yield. The all-cis structure of 4 was confirmed by X-ray analysis.

An attempt to attach the lower side chain by Mukaiyama reaction with 2-acetoxy-1-heptene gave 5 as the major product. The same product was made in 95% yield by treating 4 with TiCl$_4$ (1.25 equiv.) and acetyl chloride (2.5 equiv.) in methylene chloride for 45 min. at 0° C. Production of 5 from 4 as well as by partial hydrolysis of 3 proves that TiCl$_4$/AcCl opened the 5-membered ring of the tetracyclic acetal 4.

Wadsworth-Emmons reaction of 5 proceeded smoothly with dimethyl 2-oxoheptylphosphonate (6 equiv.) and n-butyllithium or sodium hydride (6 equiv.) in DMSO for approximately 3 hours at 50° C., giving a mixture of hydroxymethyl-enones 6a/b which were isolated by flash chromatography in 73% yield. Separately (hplc) or together 6a and 6b were oxidized by short (60 sec.) exposure to Jones' reagent in refluxing acetone to a crude, unstable carboxylic acid (7), which was decarboxylated without further purification by refluxing in glacial acetic acid, to give 1a ($[\alpha]_D^{25}$ −28° (chloroform)), as an oil in 74% overall yield (from 6a/b mixture).

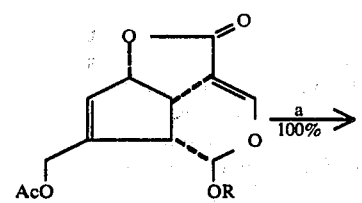

2a R = β-D-glu
2b R = β-D-gluAc$_4$

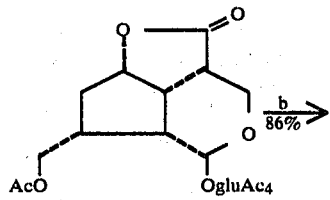

3

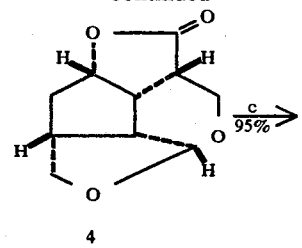

4

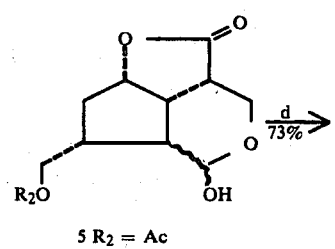

5 R$_2$ = Ac

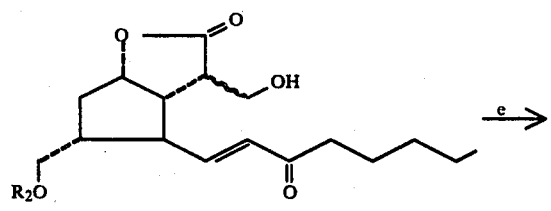

6

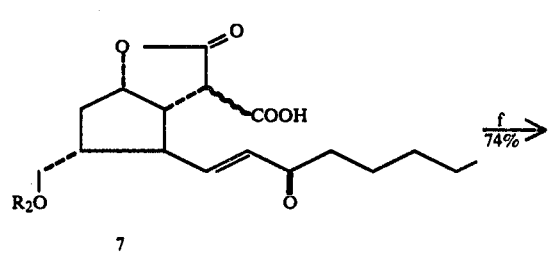

7

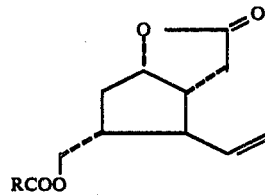

1a R = —CH$_3$
1b R = —C$_6$H$_5$

Ohno has shown that a reduced form of 1b, wherein the lactone carbonyl (C-6) has been partially reduced to a hemiacetal, is condensed with Wittig reagent derived from (4-carboxybutyl)-triphenyl-phosphonium bromide and sodium methyl sulfenylmethide in dimethyl sulfoxide followed by hydrolysis using acetic acid: water (2:1) at 40° C. afforded 35% yield of 11-deoxy-11α hydroxy methyl PGF$_{2\alpha}$. 1a should serve equally well in these reactions as 1b.

Prostaglandins are used in abortions and induction of labor. Successful clinical studies with a variety of prostaglandins and related analogs as gastric antisecretary agents, bronchodilators and agents for treating cardiovascular disease are appearing with increasing frequency.

DETAILED DESCRIPTION OF THE INVENTION

The following examples illustrate the invention.

Melting points were determined on a Thomas Hoover melting point apparatus and are uncorrected. IR spectra were recorded on Perkin-Elmer model 237B or 598 using 0.1 mm NaCl solution cells. The proton NMR spectra were determined at 60 MHz with a Varian model EM-360. High field NMR were obtained at the Southern New England High Field NMR Facility at Yale University (270 Hz) or at Columbia University (250 MHz). The chemical shifts are expressed in $\delta$ values (part per million) relative to Me Si internal standard. Mass spectra were determined at 70 ev using a Varian MAT CH-5 for medium resolution, an AEI MS-9 for high resolution, and the services of Dr. Frank Field of Rockefeller University for chemical ionization mass spectrometry. Optical rotations were measured with a Perkin-Elmer model 141 polarimeter.

All gas chromatographic analysis were carried out on a Varian Aerograph series model 920 gas chromatograph equipped with a thermal conductivity detector and helium as the carrier gas (flow rate 120 ml/min at ambient temperature) using a (10 ft.$\times \frac{3}{8}$ in) column packed with 20% Apizeon-L on chromosorb-W. Silica gel precoated glass plates (E. Merck, 1563-9H) were used for thin layer chromatography (TLC). Silica gel (E. Merck-60, 9385) was used for flash or column chromatography. TLC plates were developed by spraying with 10% methanolic sulfuric acid and heating on a hot plate. High Pressure Liquid Chromatography (HPLC) analyses were performed on Waters Associates microporasil columns (two 4 mm$\times$30 cm silica 10 columns in series) using Waters Associates 600-SDS pump, U-6k injector equipped with a model 401 index of refraction detector. HPLC preparations were conducted on a Waters Associates Pre-500 LC with two silica columns in series. The starting material, asperuloside, was purified using a 10 cm diameter column obtained from Glencoe (Houston, Tex.). The solvent was delivered to the column from a stainless steel reservoir under 6 psi of air pressure. Concentration of large quantities of liquid was most efficiently done using a "Cyclone" circulatory evaporator (Scientific Glass Apparatus Co., Bloomfield, N.J., Cat. No. JD 9350) at water pump pressure.

Methylene chloride and dimethyl sulfoxide were distilled (DMSO in vac) from calcium hydride and kept over freshly activated molecular sieves of type 4A for at least 48 hours prior to use. Sodium hydride was employed as a 57% oil dispersion which was washed with dry hexane immediately before use. For all anhydrous reactions performed undder an atmosphere of dry $N_2$ or Ar, the equipment was dried in the oven at 120 C. for 1 hour prior to use.

All micro analysis were performed by Spang Microanalytical Laboratories, Eagle Harbor, Mich. or Gailbraith Laboratories, Knoxville, Tenn.

EXAMPLE 1

Extraction of Asperuloside Using Duff's Procedure (2a)

Coprosma repens plants (17.7 Kg) were chopped and boiled with 32 L of water for one hour. The liquid was decanted and the residue was extracted with the same amount of water. The combined extracts were concentrated to 2 L and adsorbed on 500 g of acid washed Celite-535.

A column was packed with 1700 g of Celite (previously mixed with 1700 mL of of butanol-saturated water and equilibrated overnight) in a 10 cm diameter column. The Celite adsorbed plant extract was put on the top of the packed column and eluted with water-saturated butanol (flow rate 90 mL/min, pressure 6 psi). The fractions showing blue spots on TLC (Rf=0.88, 0.73; 2/1 95% ethanol-acetone) were collected and concentrated to give 140 g of brown gum.

For acetylation, 78.5 of this gum was mixed with 195 mL (2.1 moles) of acetic anhydride, stirred mechanically for 35 hours, then diluted with 30 mL (0.4 mole) of pyridine and stirred for an additional 24 hours.

The reaction was quenched by pouring into ice/water and the aqueous mixture was extracted with chloroform (3$\times$300 mL). The chloroform extracts were combined and washed with 5% aqueous HCl followed saturated aqueous sodium carbonate and, finally water. The organic extracts was then dried over anhydrous magnesium sulfate, filtered and concentrated to give 64.9 g of yellow gum.

50 g of this gum was purified by silica gel column chromatography (17" long$\times$1.7" diameter) using 3/2 ethyl acetate-hexane as the eluting solvent. This afforded 22.6 g of crude asperuloside tetraacetate as an oil. The crude product on crystallization from absolute ethanol which gave 10.3 g of pure asperuloside tetraacetate, mp 148°–150° C. The analytical sample was recrystallized from absolute alcohol, mp 150°–151° C. (lit mp 154° C.). The yield was about 0.13–0.15% based on the weight of fresh plant material committed for extraction. NMR and IR data were the identical with the literature data and with that of asperuloside tetraacetate prepared from an authentic sample of asperuloside given to us as a gift by Dr. Bobbitt.

Analysis calculated for asperuloside tetraacetate ($C_{26}H_{32}O_{15}$): C 53.60, H, 5.22. Found: C, 53.60; H, 5.20.

EXAMPLE 2

Extraction of Asperuloside Using Hot Acetone Method

One hundred grams of fresh coprosma plant cuttings were refluxed with 2 L of acetone for two hours. The acetone extract was filtered and the residue washed with 200 mL of acetone which was combined with the acetone extract. The combined acetone extracts on concentration gave 4.9 g of green gum. The green gum was adsorbed on 20 g of silica and loaded on the top of silica column (10" long$\times$1.5" diameter). The column was theen eluted, first with acetone, and then with absolute ethanol. The fractions giving blue spots on TLC (2/1 95% ethanol/acetone, compared side by side with an authentic sample of asperuloside) on concentration gave 480 mg (0.48%) of asperuloside and 250 mg (0.25%) of slow-asperuloside (probably asperulosidic acid).

However, on larger scale (20 Kg), fresh plants were boiled twice with 50 gallons of acetone (most kindly done by international Flavors and Fragrances, New Jersey and by McNeil Laboratories, Pennsylvania). The acetone extract was concentrated and dried in vacuo to give approximately 400 g of brown gum. This gum (78 g) was mixed with 500 mL of ether and left for a week after which the ether extract was decanted. The process was repeated once again which removed most of the chlorophyll. The residue was dried in vacuo to give 65 g of brown gum which was acetylated (acetic anhydride/pyridine) without further purification. The crude acetylated product (58 g) was partially purified by placing on a (6" long×2" diameter) silica column and eluting it with 1.5 L of ethyl acetate which on concentration gave a yellow gum (50 g).

Final purification of the acetylated product was achieved by a combination of high pressure liquid chromatography (1/1 ethyl acetate/hexane) and crystallization (absolute alcohol), affording 6.3 g (approx. 0.2%), mp 148-150 C. of pure asperuloside tetraacetate.

EXAMPLE 3

Preparation of Tetrahydroasperuloside Tetraacetate (3)

Asperuloside tetraacetate (14.13 g, 24.3 mmol), 13.9 g of 5% Rh/C (from Engelhard) and 2 L of ethyl acetate (either distilled or HPLC grade) were placed in a three neck, 5 liter round bottom flask connected to hydrogen reservoir and fitted with a closed system magnetic stirred. The flask was cooled to −30° C., filled with hydrogen. Stirring was commenced and the temperature was allowed to rise to 0° C. during a period of 3 hours. The solution was then filtered and concentrated to give 15.4 g (100%, one spot on TLC, Rf=0.35, 4/1 ether-ethyl acetate; one peak at 6.6 min on HPLC: 2/1 ethyl acetate/hexane) of tetrahydroasperuloside tetraacetate as a white foamy solid. Recrystallization gave 11.3 g (80%), mp 148°-9° C. of pure tetrahydroproduct. The crude material, however, could be used directly for hydrolysis. It was found that the used catalyst works as well as the new one and was used over and over again. NMR(CDCl): C(3)=3.89 (2H,m); C(5)=δ3.74 (1H,ddd); C(6)=δ5.03 (1H,m); C(8)=δ2.35 (1H,dd,J=8,10.5) becomes sharp when irradiated at C(1)[δ5.4], doublet (J=10.5) when irradiated at C(8)[δ2.6], doublet (J=8) when irradiated at C(5)[δ3.7].

Analysis calculated for $C_{26}H_{36}O_{15}$: C,53.24; H,5.50. Found: C,53.48; H,5.83.

EXAMPLE 4

Preparation of Tetracyclic Acetal 4 By Hydrolysis of Tetrahydroasperuloside Tetraacetate with 5/1 Acetic Acid-Water.

A solution of 14.72 g of tetrahydroasperuloside tetraacetate 3 was refluxed in 5/1 acetic acid-water (100°-115° C.) for 12 days. The resulting mixture was concentrated on the rotavap and the residue was dried in vacuo to give a brown gum. To this was added 400 mL of water and 200 mL of chloroform and the mixture was vigorously shaken. The organic layer was separated and the aqueous extract was extracted again with chloroform (2×200 mL). All the organic extracts were combined and washed with water, dried over anhydrous magnesium sulfate, decolorized with carbon and concentrated to give 4.76 g of white solid (mp 103°-6° C.). The solid was crystallized from chloroform/ether to 4.23 g of tetracyclic acetal, mp 111°-3° C. (anal. mp 113°-114° C.).

In general, refluxing was continued for 8-12 days and the acetal was isolated in 86-92% yield.

IR: 1773 cm$^{-1}$ (5-membered lactone). Mass Spectra: A peak at m/e 196 (M, 20). Optical rotation: $[\alpha]_D^{25} -61.5$ C. (c 0.036, chloroform).

EXAMPLE 5—X-Ray Analysis

The all cis-structure (FIG. 4) was confirmed by X-ray analysis most kindly performed by Dr. John Blount of Hoffmann-LaRoche (Nutley, N.J.). The crystals were trigonal, space group $P3_2$.

EXAMPLE 6

Preparation of Tetracyclic Acetal 4 by Hydrolysis of Tetrahydroasperuloside Tetraacetate with Acetone and Acid Tetrahydroasperuloside tetraacetate (128 mg, 0.22 mmol) was refluxed with 20 mL of acetone and 0.12 mL of sulfuric acid for 19 hours. The reaction was quenched by pouring it into 25 mL of water. The water solution was extracted with chloroform (2×25 mL) and the combined organic extracts were washed with water and 5% aqueous sodium bicarbonate. The organic extract was then dried over magnesium sulfate, concentrated and dried in vacuo to give 217 mg of brown oil.

The tetracyclic acetal was isolated from this brown oil by column chromatography on a silica gel column, eluting first with ether and then with 4/1 ether-ethyl acetate, affording pure tetracyclic acetal 4 (19.4 mg, 43%), mp 112°-3° C. The IR, NMR and mp were identical with the previous sample obtained by refluxing tetrahydroasperuloside tetraacetate in 5/1 acetic acid-water.

Analysis calculated for $C_{10}H_{12}O_4$: C,61.22; H,6.16. Found: C,61.05; H,6.15.

EXAMPLE 7

Preparation of Diacetoxy Aglucone:Hydrolysis Tetrahydroasperulosidete Traacetate Using Acetic Anhydride/Acetic Acid/H+

Acetic anhydride (20 mL, 21.6 g, 0.22 mole), 0.5 mL water and 0.5 mL conc. sulfuric acid were mixed and stirred for 30 minutes. To this mixture was added 485 mg (0.83 mmol) of tetrahydrasperuloside tetraacetate and stirring was continued for additional 1 day. The reaction was quenched by pouring this mixture into 50 mL of ice cold water. The aqueous mixture was extracted with chloroform (2×50 mL). The organic extract was washed with saturated aqueous sodium bicarbonate followed by 25 mL of water, and then dried over anhydrous magnesium sulfate and concentrated to give 335 mg of white gum. Three components of this gum were separated using column chromatography (4/1 ether-ethyl acetate) to give 193 mg (60%) of glucose pentaacetate and 90 mg (a major mp 112°-114° C. and a minor component) of diacetoxy aglucone (analytical sample mp 114°-115° C. was recrystallized from ether/chloroform). It was found that the isolated yield of diacetoxy aglucone varied (0-65%), TLC examination showed that part of it hydrolysed during workup to give hemiacetal 5.

Analysis calculated for $C_{14}H_{18}O_7$: C, 56.37; H, 6.08. Found (major component): C, 56.13; H, 5.92.

EXAMPLE 8

Preparation of 2-Acetoxy-1-Heptene

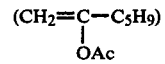

USING HUDRLIK'S PROCEDURE

A mixture of 110 mL of acetic anhydride, 197 mg of mercuric acetate and 0.3 mL of boron trifluoride etherate was stirred for 5 minutes. To this mixture 7.33 g (76.3 mmol) of 1-heptyne was added and stirring was continued for an additional 3 hours.

The reaction was quenched by pouring into a 20% potassium hydroxide solution (1000 mL) overlayed with 700 mL of ether (precooled to 0° C.). The layers were separated and the ether layer was washed with brine solution, dried over anhydrous magnesium sulfate and the ether was evaporated. The residue was distilled bulb to bulb (1 atm) to give 5.9 g of colorless oil. Pure 2-acetoxy-1-heptene was isolated by gas chromatography. The fraction with retention time Rt=21.0 min. was collected. Multiple injections afforded to 4.35 g of the product (36.5% yield).

NMR (CDCl$_3$): $\delta$0.9(3H,t), $\delta$2.1(3H,s), $\delta$4.5-4.6(2H); Lit. NMR ($\phi$H):$\delta$1.75(3H), $\delta$4.59,4.78(2H,m).

EXAMPLE 9

Partial Hydrolysis of Tetrahydroasperuloside Tetraacetate Using 5/1 Acetic Acid-Water Tetrahydrasperuloside tetraacetate (4.5 g), 200 mL of acetic acid and 40 mL of water were mixed in a 500 mL round bottom flask fitted with a magnetic stirrer and a refluxing condenser. The temperature was raised from room temperature to 90° C. over a period of 1 hour and then maintained at 90°-100° C. for an additional 1.5 hours.

The mixture was concentrated in the rotavap and the residue was dried in vacuo to give 4.4 g of white foamy solid. TLC examination showed it to contain glucose pentaacetate (Rf=0.59), tetrahydroasperuloside tetraacetate 6 (Rf=0.51), tetracyclic acetal 4 (Rf=0.37) and hemiacetal 5 (Rf=0.26) when developed in 2/3 methylene chloride-ethyl acetate. The hemiacetal 5 was isolated from this mixture by column chromatography (10" long×1.5" diameter) silica gel (230-400 mesh) column using 2/3 methylene chloride-ethylacetate as the eluting solvent. Concentration of the last fraction gave 703 mg (36.1%) of hemiacetal 5 (mp 140°-145° C.). Double crystallization of this mixture gave 195 mg (mp 151°-2° C.) of analytical sample.

NMR: $\delta$2.0(3H,s,acetate). IR: 1770 cm (5-membered lactone), 1738 cm$^{-1}$ (acetate), 33-3600 cm$^{-1}$ (—OH).

Analysis calculated for C$_{12}$H$_{16}$O$_6$: C, 56.35; H, 6.29. Found: C, 55.98; H, 4.46.

EXAMPLE 10

Preparation of Hemiacetal 5 by Treating Tetracyclic Acetal 4 with Titanium Tetrachloride and Isopropenyl Acetate A solution of 1% (3.1 mL, 1.1 eq.) titanium tetrachloride in dry methylene chloride and 7 mL (2.5 eq.) of a 1% solution of isopropenyl acetate in dry methylene chloride were mixed at −15° C. in a 25 mL round bottom flask under argon atmosphere. To this mixture was added 50 mg (0.255 mmol) of tetracyclic acetal 4 in 2 mL of dry methylene chloride, dropwise over a period of 10 minutes. The resulting mixture was stirred for 2 hours, during which the temperature rose to −5° C. A further 10 mL (3.6 eq.) of 1% titanium tetrachloride solution was added and the mixture was stirred for one more hour at −5° C.

The reaction was quenched by adding 450 mg of solid sodium bicarbonate and 4 drops of water and was stirred for 0.5 hour during which chunky titanium dioxide precipitated. On filtration and concentration gave 56 mg (86%) of organic substances containing a major (Rf=0.20) and a minor (Rf=0.64) components (TLC, 3/2 methylene chloride-ethyl acetate). The major component was separated by crystallization from methylene chloride-ethyl acetate, affording 32 mg (49%) of white crystals, mp 115°-6° C. When recrystallized from ethyl acetate-methanol, this material afforded a new compound mp 147°-9° C. but with no change in R$_f$(=R$_f$of 5).

Analysis calculated for C$_{12}$H$_{16}$O$_6$: C, 56.25; H, 6.29. Found: C, 56.34; H, 6.27.

EXAMPLE 11

Preparation of Hemiacetal 5 by Treatment of Tetracyclic Acetal 4 with Titanium Tetrachloride and 2-Acetoxy-1-Heptene Tetracyclic acetal 4, 100 mg (0.51 mmol) was dissolved in 1 mL of methylene chloride in a 25 mL round bottom flask with a magnetic stirred under an argon atmosphere at −10° C. To this solution, 148 mg (1.9 eq.) of 2-acetoxy-1-heptene in 2 mL of methylene chloride was added. To this was then added 8 mL (1.5 eq.) of a 1% solution of titanium tetrachloride in methylene chloride dropwise over a period of 10 minutes, and the resulting mixture was stirred for 2 hours. During this period the temperature rose to +15° C.

The reaction was quenched by adding 365 mg of solid sodium bicarbonate and 4 drops of water and stirring for 0.5 hour, during which chunky titanium dioxide precipitated. The solution was dried over anhydrous potassium carbonate and filtered. The residue was washed with ethyl acetate, the wash was combined with the filtrate and evaporated to give 115 mg of white solid (mp 136°-7° C.). The white solid was crystallized from ethyl acetate/methanol, which afforded 64 mg of white crystals (mp 147.5°-149° C.).

Analysis calculated for C$_{12}$H$_{16}$O$_6$: C, 56.25; H, 6.29. Found: C, 56.23; C, 6.26.

EXAMPLE 12

Preparation of Hemiacetal 5 by Treating Tetracyclic Acetal 4 with Titanium Tetrachloride/Acetyl Chloride A solution of 1.0002 g (5.1 mmol) of tetracyclic acetal 4 in 80 mL of dry methylene chloride was placed in a 250 mL three neck round bottom flask fitted with a magnetic stirrer, refluxing condenser and a dropping funnel under an argon atmosphere and surrounded by ice/water mixture. To this flask was then added 4.6 mL (12.95 mmol, 2.5 eq.) of a 20% solution of acetyl chloride in dry methylene chloride, followed by 7.0 mL (6.5 mmol, 1.25 eq.) of a 10% solution of titanium tetrachloride in dry methylene chloride diluted with 20 mL of dry methylene chloride, added dropwise over a period of 10 minutes. During the addition of titanium tetrachloride solution, the reaction mixture turned pale yellow. The reaction mixture was stirred for an additional 45 minutes.

The reaction was quenched by adding 5 g of potassium carbonate, 100 mL of methylene chloride and 2 mL of water and stirring for 2 hours. During this time chunky titanium dioxide precipitated and carbon dioxide gas was evolved. The resulting mixture was decanted, dried over anhydrous potassium carbonate and filtered. The residue was boiled with 100 mL of ethyl acetate, filtered and combined with the previous filtrate. The combined filtrates were concentrated, and the resulting residue was dried in vacuo to give 1.24 g (95%) of white solid, mp 122°-8° C., which on crystallization from ethyl acetate gave 1.08 g of hemiacetal 5, mp 144°-7° C. (anal. mp 149°-151° C.).

NMR and IR spectra were identical with those obtained from the product of partial hydrolysis of tetrahydroasperuloside tetraacetate with acetic acid/water.

EXAMPLE 13

Preparation of Benzoate by Treatment of Tetracyclic Acetal 4 with Titanium Tetrachloride/Benzoyl Chloride A solution of 50 mg of tetracyclic acetal 4 (0.255 mmol) and 0.22 mL (0.379 mmol, 1.5 eq.) of benzoyl chloride in mL of dry methylene chloride and 0.35 mL (0.318 mmol, 1.25 eq.) of titanium tetrachloride were mixed at 0° C. The temperature of the mixture was allowed to rise to room temperature and stirring was continued for a total of 42 hours.

The reaction was quenched by adding 15 mL of methylene chloride, a few drops of water and 500 mg of potassium carbonate and stirring for three hours. The mixture was the dried over anhydrous potassium carbonate, filtered and concentrated to give 82.2 mg of brown gum. This brown gum was loaded on the top of silica column (7" long × 1.5" diameter) and eluted with 3/2 ethyl acetate-hexane. The eluent was concentrated to give 58.6 mg (white gum) of 5b (74%) which on crystallization gave 14.9 mg (mp 129.5°–131° C.) of white solid.

NMR: $\delta 7.3–8.2$ (5H,m), $\delta 6.5$ (1H). IR: 1776 cm$^{-1}$ (5-membered lactone).

Analysis calculated for $C_{17}H_{16}O_5$: C, 67.99; H, 5.73. Found: C, 67.53; H, 5.50.

EXAMPLE 14

Preparation of Enone 6 Using Wittig Reaction n-Butyllithium 10.4 mL (16.7 mmol, 1.6 M in hexane) was added dropwise to a 20 mL of dry dimethylsulfoxide under a nitrogen atmosphere and stirred for 20 minutes. To this dimethylsulfoxide solution, 3.6 mL (17.4 mmol) of dimethyl 2-oxo-heptyl phosphonate was added dropwise during 5 minutes and the mixture was stirred for additional 15 minutes. Hemiacetal 5, 724.4 mg (2.83 mmol) in 3 mL of dry dimethylsulfoxide was then injected at room temperature. The flask containing the 5 was rinsed with two two mL portions of dimethylsulfoxide which were also added to the reaction mixture. The temperature of the reaction mixture was then raised to 50° C. over a period of 0.5 hour and maintained at 50°–55° C. for an additional 3 hours.

The reaction mixture was then cooled to room temperature and quenched by adding 3.4 mL of glacial acetic acid, poured into 100 mL of water and extracted with 3×75 mL of methylene chloride. The combined organic extracts were washed with 50 mL of water which was back extracted with 50 mL of methylene chloride. The back wash was combined with the original organic extract, dried over anhydrous magnesium sulfate, filtered and concentrated. The residue was dried in vacuo for 4 hours at 100°–110° C., giving 1,409 g of brown gum.

This brown gum was chromatographed on a silica column (9" long × 1.5" diameter), eluting with 600 mL of 2/1 ethyl acetate-hexane. The eluent was concentrated to 774 mg (73.7%) of a mixture of enones 6 a, b (major: 6.6 min; minor: 8.3 min in approx. 8/1 ratio, on HPLC: 2/1 ethyl acetate-hexane, 2 mL/min) as a yellow gum.

Analysis calculated for $C_{19}H_{28}O_6$: C, 64.75; H, 8.01. Found (major): C, 64.64; H, 8.09. (minor): C, 64.04; H, 8.23. The analysis of the minor component was not repeated due to insufficient material.

EXAMPLE 15

Preparation of Carboxylic Acid 7

Jones reagent (4 mL) was added drop by drop to 16 mL of acetone maintained at reflux by an oil bath at 59°–60° C. To this refluxing mixture, a solution of 173.6 mg (0.49 mmol) of alcohol 6 in 5 mL of acetone was injected over a period of 10 seconds and refluxing was continued for an additional 50 seconds.

The reaction was then quenched by adding excess isopropanol (10 mL), poured into 200 mL of water and extracted with ether (4×100 mL). The combined organic extracts were dried over anhydrous magnesium sulfate, filtered and concentrated and the residue dried in vacuo to give 168 mg (0.46 mmol, >90%) of crude carboxylic acid 7 which was used for decarboxylation without further purification.

EXAMPLE 16

Preparation of Enone 1a

Crude carboxylic acid 7 (168 mg, 0.46 mmol) was refluxed with 100 mL of glacial acetic acid for 3.5 hours. The mixture was concentrated and dried in vacuo to give a brown gum. This brown gum was dissolved in 10 mL of methylene chloride and poured over the top of 1" thick layer of silica gel in a sintered glass funnel and eluted with 100 mL of methylene chloride followed by 100 mL of ethyl acetate. The combined filtrates were concentrated and dried in vacuo to give 115.3 mg (0.36 mmol, 78%) of white gum, one spot on TLC (Rf=0.51, 1/1 ethyl acetate-hexane) and one peak on HPLC (7.3 min. 1/1 ethyl acetate-hexane). The product 1a was isolated in 72–74% overall yield for oxidation and decarboxylation.

H NMR: (250 MHz, CDCl$_3$): $\delta 6.183$(1H,d,J=15.6), $\delta 6.613$(1H,dd,J=15.6,8.6), $\delta 2.024$(3H,s), $\delta 4.05$, 4.16(2H,dd), $\delta 4.974$(1H,m), $\delta 2.518$(2H,t,J=7.4), $\delta 0.886$(3H,t,J=6.8), $\delta 1.286$(2H,m). IR: 1767, 1733, 1689, 1629 cm$^{-1}$.

Analysis calculated for $C_{18}H_{26}O_5$: C, 67.06; H, 8.13. Found: C, 67.14; H, 8.14.

We claim:

1. A process for the synthesis of prostaglandin intermediates from iridoids comprising the steps of:
   (1) forming a tetraacetate of a C-1 glycoside a 10 carbon aglucone;
   (2) hydrogenating the tetraacetate to eliminate all olefinic double bonds and form tetrahydroaglucone glycoside tetraacetate;
   (3) forming an acetal between C-1 and C-10 by hydrolysis;
   (4) treating the acetal with titanium tetrachloride and acetyl chloride or an enol acetate to open the five membered ring of the tetracyclic acetal forming an hydroxyl in the C-1 position;
   (5) applying Wadsworth-Emmons reaction to the hydroxyl compound formed in Step (4) to produce a 3-oxo-1[E]-octenyl chain at the C-1 position and opening the ring at the 0-2 and C-1 positions and having an hydroxyl group at C-3; and
   (6) oxidizing the hydroxyl to carboxylic acid with Jones reagent and decarboxylating the carboxylic acid to produce a prostaglandin intermediate.

2. A process of claim 1 wherein the aglucone is selected from the group consisting of Asperuloside, deacetylasperuloside, paederoside, scandoside, daphylloside and paederosidic acid.

3. A process for the synthesis of prostaglandin intermediates from asperuloside comprising the steps of:
(1) converting the asperuloside to a tetraacetate at the C-1 glucose site;
(2) hydrogenating the tetraacetate to hydrogenate completely all olefinic double bonds and produce tetrahydroasperuloside tetraacetate;
(3) hydrolyzing the tetrahydroasperuloside tetraacetate for a sufficient time to produce a tetracyclic acetal between C-1 and C-10;
(4) reacting the tetracyclic acetal with titanium tetrachloride and acetyl chloride to open the five membered ring of the acetal formation and forming an hydroxyl in the C-1 position;
(5) reacting the hydroxyl group with dimethyl 2-oxoheptylphosphonate and n-butyllithium or sodium hydride to give a mixture of hydroxymethyl-enones; and
(6) oxidizing the enones to an unstable carboxylic acid and decarboxylating the acid to give a prostaglandin intermediate of [3aR,4S,5R,6aS]-hexahydro-5-(hydroxymethyl)-4-[(E)-3-oxo-1-octenyl]-2H-cyclopenta[b]furan-2-one acetate.

* * * * *